United States Patent [19]

Sato et al.

[11] Patent Number: 5,223,255
[45] Date of Patent: Jun. 29, 1993

[54] BORDETELLA PERTUSSIS VARIANTS

[75] Inventors: Yuji Sato; Hiroko Sato, both of Tokyo; Iwao Yoshida, Kanonji; Atsushi Imaizumi, Hino, all of Japan

[73] Assignees: Teijin Limited, Osaka; National Institute of Health, Tokyo, both of Japan

[21] Appl. No.: 774,637

[22] Filed: Oct. 11, 1991

Related U.S. Application Data

[63] Continuation of Ser. No. 209,599, Jun. 22, 1988, abandoned.

[30] Foreign Application Priority Data

Jun. 24, 1987 [JP] Japan ................................ 62-155577

[51] Int. Cl.$^5$ ........................ A61K 39/02; C12P 21/04
[52] U.S. Cl. ............................. 424/92; 424/88; 530/350; 435/70.1; 435/71.1; 435/71.2; 435/243; 435/244; 435/822; 435/252.1
[58] Field of Search .................. 424/92, 93, 88; 530/350; 435/70.1, 71.1, 71.2, 243, 244, 822

[56] References Cited

U.S. PATENT DOCUMENTS 4,687,738 8/1987 Ginnaga et al. ..................... 435/68

OTHER PUBLICATIONS

Marchitto et al, *Infection and Immunity*, vol. 55, No. 5, pp. 1309–1313, May 1987.
Perera et al, *Journal of General Microbiology*, vol. 133, pp. 2427–2435, 1987.
Patent Abstracts of Japan, vol. 8, No. 67 (C-216)[1504], Mar. 29, 1984; and JP-A-58 222 032 (Teijin K.K.) Dec. 23, 1983.
A. C. Wardlaw and R. Parton, Pharmac. Ther. vol. 19, 1–53, 1983.
Y. Sato, M. Kimura and H. Fukumi, The Lancet, Jan. 21, 122–126, 1984.
C. Locht and J. M. Keith, Science, vol. 232, 1258–1264, 1986.

*Primary Examiner*—Michael G. Wityshyn
*Assistant Examiner*—Abdel A. Mohamed
*Attorney, Agent, or Firm*—Sughrue, Mion, Zinn, Macpeak & Seas

[57] ABSTRACT

A Bordetella pertussis variant which produces a pertussis toxin mutant protein partially devoid of subunits. When the variants of the present invention are cultured, a pertussis toxin mutant protein partially devoid of subunits, particularly at least subunit S1, can be harvested from the culture. The thus-obtained pertussis toxin mutant protein partially devoid of subunits can be applied to the preparation of a pertussis vaccine by a conventional method.

6 Claims, 4 Drawing Sheets

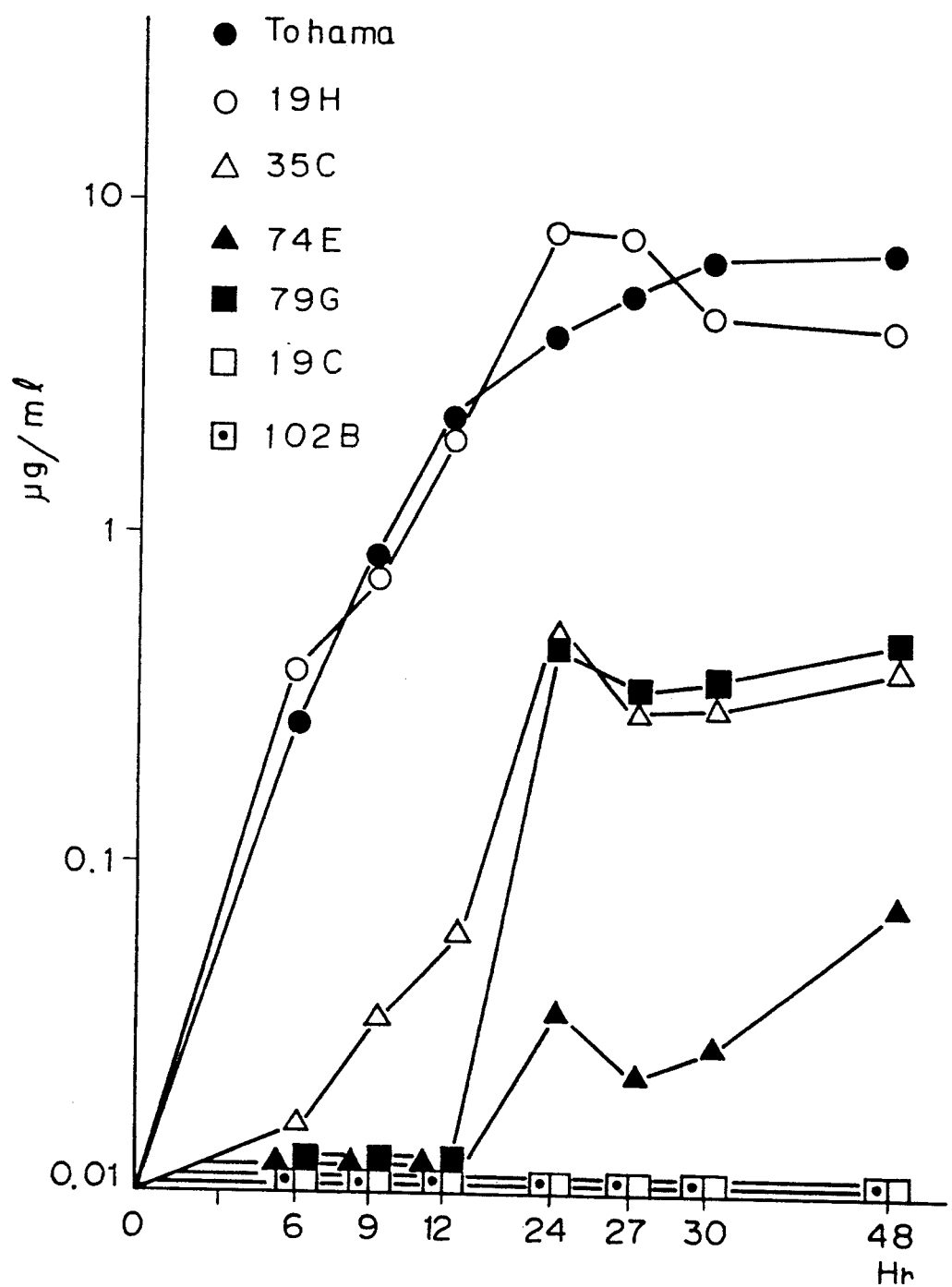

1: PT (Tohama)
2: 79G-PTMP

1: PT (Tohama)
2: 79G-PTMP

BORDETELLA PERTUSSIS VARIANTS

This is a continuation of application Ser. No. 07/209,599, filed Jun. 22, 1988, now abandoned.

BACKGROUND OF THE INVENTION

1. Field of the Invention

The present invention relates to Bordetella pertussis variants producing a non-toxic but immunogenic pertussis toxin mutant protein, which is applied for preparing a new pertussis vaccine.

More particularly, the present invention relates to a Bordetella pertussis phase I variant not having a pertussis toxic activity, but producing a partial antigen protein which induces an antibody for neutralizing the biological activity of pertussis toxin.

2. Description of the Related Art

The pertussis toxin has a molecular weight of about 107 KDa, and is composed of two functionally different parts (A and B) as the bacterial toxin, such as diphtheria toxin and cholera toxin. The part A (subunit 1, S1) is thought to be involved in NAD-dependent ADP-ribosyltransferase activity, and part B (subunit 2, 3, 4(2), 5, S2, S3, S4, S5) is involved in the binding to target cells. A variety of the following physiological activities thereof are known: namely, leukocytosis-promoting activity, histamine sensitizing activity, islet-activating activity, adjuvant activity, mitogen activity, glycerol-releasing activity, vascular permeability stimulating activity, and CHO cell-clustering activity. Based on these physiological activities, pertussis toxin is considered a major pathogenic factor in the occurrence of whooping cough, an infection having a serious effect on infants. Accordingly, pertussis toxin is recognized as an important protective antigen in the preparation of a corresponding pertussis vaccine.

In general it is important that toxic activity thereof is eliminated and the antigenicity thereof is maintained, to ensure the safety when preparing a pertussis vaccine consisting of such a toxic protein, and accordingly, the toxin is detoxified (i.e., toxoid formation) with agents such as formalin or glutaraldehyde, which modify the lysine residue. Recent reports of the gene cloning of pertussis toxin have demonstrated, however, that no lysine residue is contained in the active (i.e., NAD-dependent ADP-ribosyltransferase) site, due to the original toxic activity, and this means that the pertussis toxin is not sufficiently inactivated by the previous toxoid formation method. It is not clear whether or not the remaining toxic activity has an effect on the human body. Therefore, to avoid the above problems, the development of a pertussis toxoid having no biological activities but inducing an antibody for neutralizing the biological activities of pertussis toxin, is required.

Recently, biotechnology, particularly gene manipulation techniques, has been used as a method for an effective mass production of useful, physiologically active proteins. As previously set forth, the gene of pertussis toxin is also cloned, and some expressions are conducted using E. coli.

Nevertheless at the present time, this pertussis toxin consists of 5 subunits, and E. coli produces the recombinant pertussis toxin inside the cells. Thus many problems in industrial production remain.

SUMMARY OF THE INVENTION

The present inventors used mutagens to obtain variants producing a toxic pertussis toxin as a means of resolving the above mentioned problems, and screened Bordetella pertussis variants producing pertussis toxin mutant protein partially devoid of subunits from among many variants, and their findings as follows, led to the present invention. The pertussis toxin mutant protein produced by the variant had a capacity of inducing an antibody which neutralizes the biological activity of pertussis toxin, and the antibody showed the same protective activity in experimental infectious model using mice in vivo as the antibody induced with pertussis toxoid.

The present invention provides a Bordetella pertussis variant which produces a pertussis toxin mutant protein partially devoid of subunits, particularly at least subunit S1. One of the variants according to the present invention is deposited in the Fermentation Research Institute, Agency of Industrial Science and Technology (1-3, Higashi 1-chome, Tsukuba-shi, Ibarakiken, Japan) with Bikoken Kinki No. 9428 (FERM P-9428) on Jun. 23, 1987, and transferred to the international deposition on Jun. 2, 1988, with FERM BP-1902.

When the variants of the present invention are cultured, a pertussis toxin mutant protein partially devoid of subunits, particularly at least subunit S1, can be harvested from the culture. Preferably, cyclodextrin or a derivative thereof is added to the medium at the time of culturing the variant. The thus obtained pertussis toxin mutant protein partially devoid of subunits is applied to the preparation of pertussis vaccine using the conventional method.

BRIEF EXPLANATION OF THE DRAWINGS

FIG. 1(c) shows the substances reacting with anti-PT antibody, with an elapse of time, respectively;

DESCRIPTION OF THE PREFERRED EMBODIMENTS

Figure 1A:
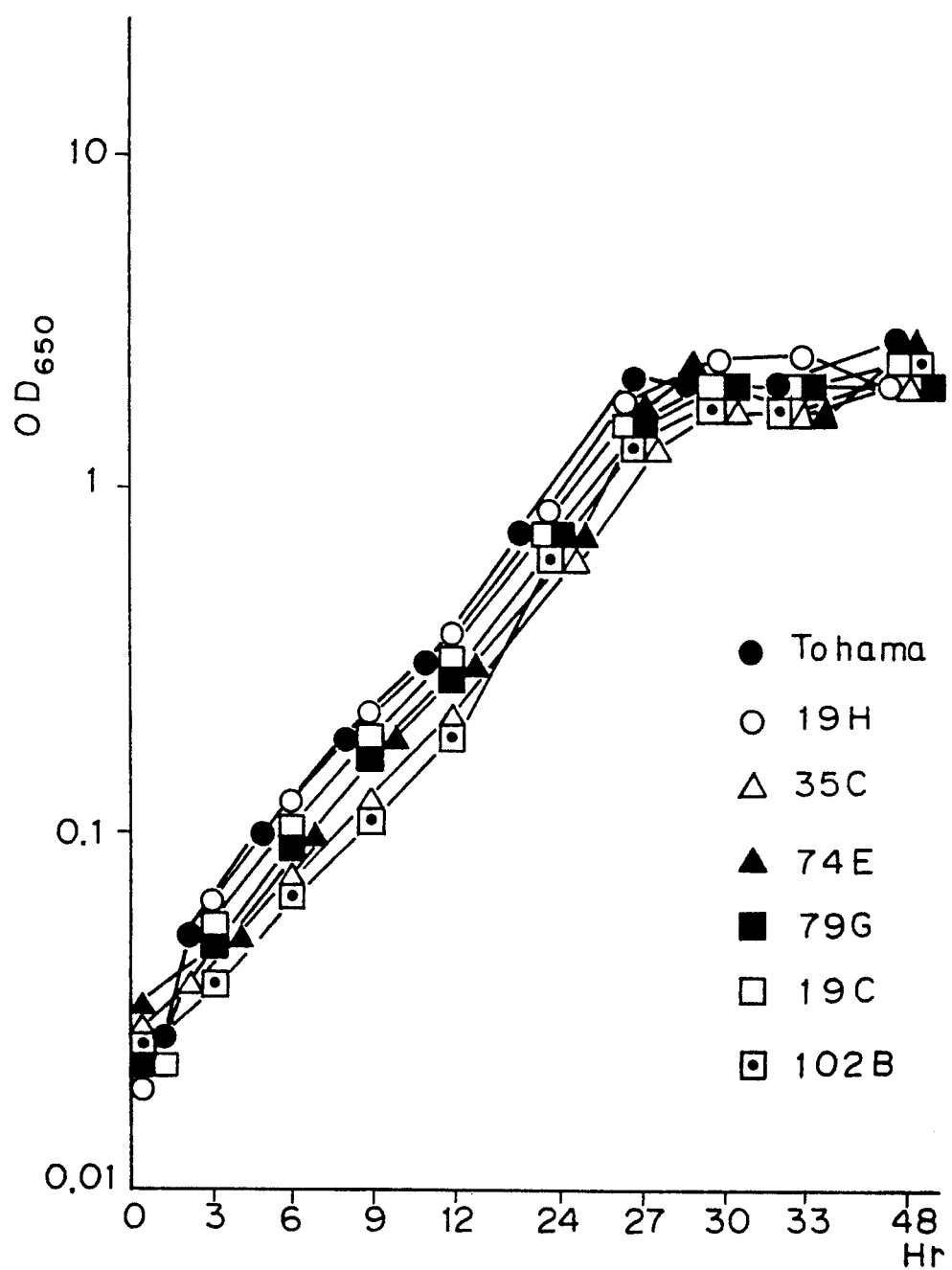
FIG. 1(a) shows changes of the growth of each variant according to the present invention in the liquid medium.
Figure 1B:
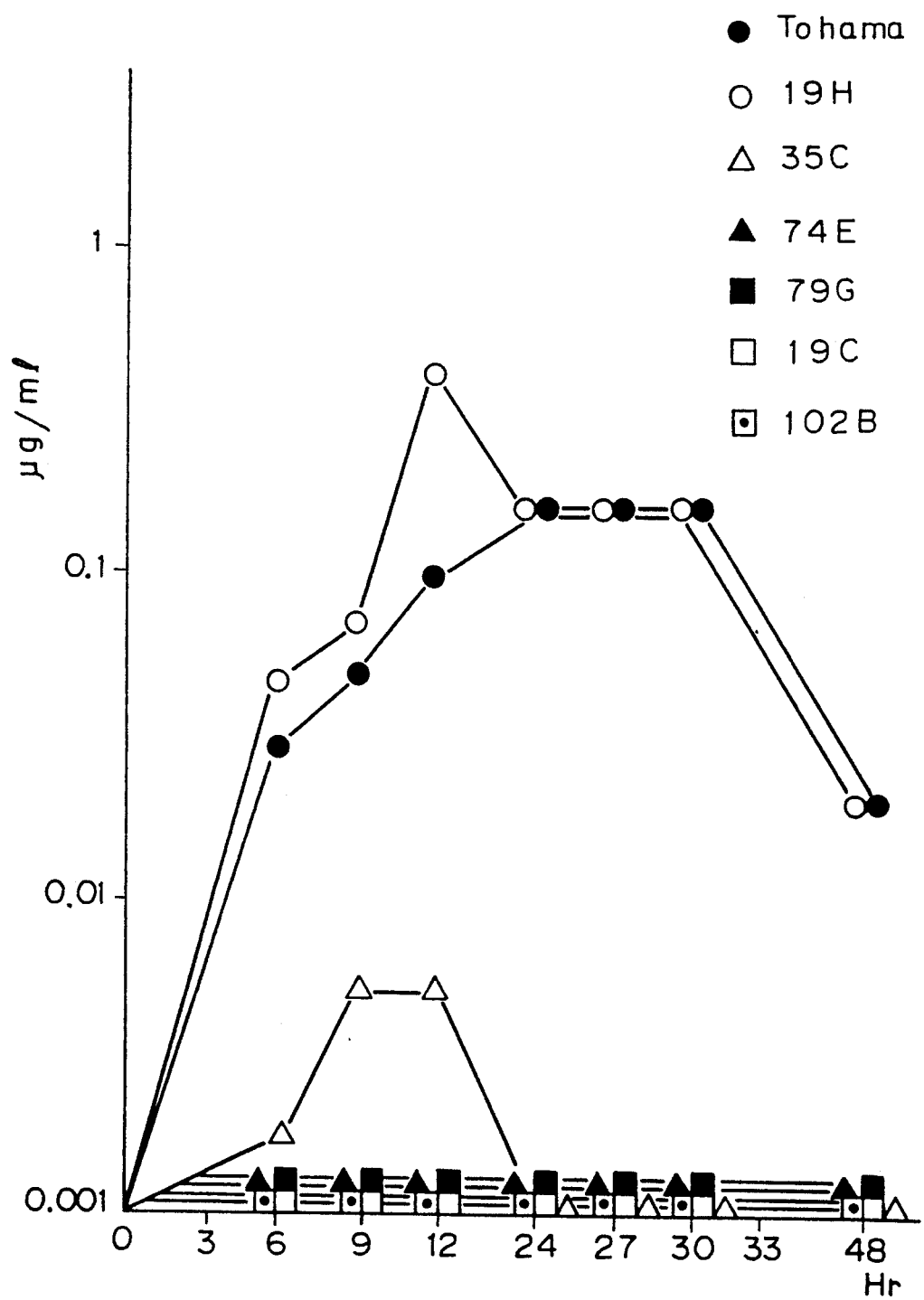
FIG. 1(b) shows CHO cell-clustering activities observed in supernatants of the cultures.

The methods of selecting the variants, the characters of the variants and the properties of the proteins produced according to the present invention are described below in detail with reference to examples.

Prior to the description of the examples, a description of the materials and methods used is given.

(1) Culture methods for Bordetella pertussis (i) Liquid culture

Bordetella pertussis Tohama phase I strain was shake-cultured in Stainer-Schalte liquid medium to which dimethyl-β-cyclodextrin (CLM) was added, at 35° C. for 36 hours.

(ii) Solid culture

A medium having a 1.5% agar solution added to the above mentioned CLM was used as the solid medium, and the Tohama strain was cultured at 35° C. for 5 to 7 days. Upon screening the above mentioned, liquid medium was shared equally among each well of a 96 wells-microplate, which was shake-cultured at 35° C. for 36 hours.

(2) Assay of CHO cell clustering activity

Since an extremely small amount of pertussis toxin (30 pg/ml) causes clustering of the CHO cells, the presence of toxic activity was screened by this method. $5\times10^3/200$ μl/well of CHO-K1 cells shared among each well of the 96 well-microplate, in which 10 μl of the supernatant of the culture medium of variant (or the standard pertussis toxin) was added, was cultured in 5% $CO_2$ at 37° C. overnight. Then, the degree of clustering, scored (3, 2, 1, 0), was observed and the activities determined in comparison with the test toxin.

(3) Assay of leukocytosis-promoting activity, islet-activating activity, and histamine sensitizing activity 0.2 ml of the sample was intravenously injected to a ddy-mouse (SPF) aged 4 weeks, and for the assay of leukocytosis-promoting activity, the peripheral leukocytes were collected and counted from the mouse after 3 days. With regard to islet-activating activity, insulin in blood collected from a mouse starved overnight and to which 0.5 ml of 30% glucose solution was intraperitoneally administered following the measurement of leukocytosis-promoting activity, were measured by RI or ELISA. The measurement of the histamine-sensitizing activity was performed by measuring the rectum temperature at 30 minutes, or determining whether the mouse intraperitoneally injected with 0.5 ml of histamine (4 mg/ml) was alive or dead after 2 hours, following the measurement of leukocytosis-promoting activity. When measuring the neutralizing activities of the antibody for these 3 activities, equal volumes of 1 μg/ml pertussis toxin and the antibodies were mixed to react at room temperature for 30 minutes or more, 0.2 ml of each mixture was intravenously injected to mice (4 weeks of age), and the neutralizing activities were calculated from the activity which was obtained by measuring the affects on each mouse.

(4) Determination of pertussis toxin and pertussis toxin mutant protein

ELISA was used for the determination, and the measurement of pertussis toxin and pertussis toxin mutant protein was performed by the conventional method using a microplate coated with poly- or monoclonal antibodies against pertussis toxin.

(5) SDS-PAGE and immunoblot

Pertussis toxin or samples treated with 0.1% SDS without reducing agents were separated on 5% stacking gel and 15% separation gel, were blotted on a nitrocellulose membrane to react with polyclonal antibodies, and were then reacted with HRPO-anti-mouse IgG and the substrates were colored.

EXAMPLE 1

The Bordetella pertussis Tohama phase I was cultured by the conventional method and collected by centrifugation. The bacteria was then suspended in a Tris-malate buffer to reach a cell concentration of $10^{10}$ cells/ml, to the suspension of which was added nitrosoguanidine as mutagen at a total concentration of 25–50 μg/ml, and the whole was shaken for 60 min. This treatment decreased the number of live bacteria to about 1/10,000. After collecting in the liquid medium by centrifugation, and an appropriate dilution with the medium in accordance with the number of the live bacteria, the bacteria was plate-cultured on the solid medium for 5 to 7 days. The colonies on the plate were picked up and seeded in the liquid medium, which was shake-cultured for 48 hours. Using the supernatant of the culture, the productivity was estimated by the CHO cell-clustering activity, and the production of the protein reacting with the antibody was detected by ELISA using an anti-pertussis toxin antibody (aPT).

About 12,000 variants of the colonies were screened and divided into the following three groups: ① negative CHO cell-clustering activity and negative $\bar{a}$PT ELISA activity; ② negative CHO cell-clustering activity and positive $\bar{a}$PT ELISA activity; ③ positive CHO cell-clustering activity and positive $\bar{a}$PT ELISA activity.

FIG. 1 shows change of growth of each representative variant in the liquid medium, CHO cell-clustering activities observed in the supernatants of the cultures, and PT antibody reacting substances, respectively, with an elapse of time. It was found that the variant 79G did not have CHO cell-clustering activity, which is one of the pertussis toxic activities, but reacted with the polyclonal antibody against pertussis toxin, as shown in FIG. 1.

EXAMPLE 2

Bordetella pertussis is characterized by the phenomenon of phase variation, wherein the wild type (i.e., the pathogenic bacteria) is called phase I bacteria, and the atoxic type is known as phase III of phase IV bacteria; this classification being based on the serotype. Then, the toxicities in mouse by intracerebral inoculation of these variants (ic toxicity), productivity of thermolabile (dermonecrotic) toxin (DNT) and serotypes of agglutinin were studied to elucidate the bacteriological characters of each variant. The results are shown in Table 1. This data demonstrates that the desired variant 79G varies to phase I bacteria, and the variant 19C and the variant 102B varied to phase III bacteria. In addition, the variant 79G is remarkably attenuated in mouse ic toxicity of $2.5\times10^7$ or more.

TABLE 1

| | ic toxicity, DNT productivity, and serotype of variants (living) | | |
|---|---|---|---|
| Strain | Virulence (ic) $LD_{50}$/mouse | DNT mm/$10^9$ | Serotype |
| 19C | $> 2.5\times10^7$ | — | 7 |
| 102B | $> 2.5\times10^7$ | — | 7 |
| 35C | $> 2.5\times10^7$ | 9 | 1, 2, 4, 7 |
| 79G | $> 2.5\times10^7$ | 11 | 1, 2, 4, 7 |
| 74E | $3.5\times10^6$ | 9 | 1, 2, 4, 7 |
| 19H | $1.0\times10^4$ | 10 | 1, 2, 4, 7 |
| Tohama (wild) | $6.3\times10^2$ | 10 | 1, 2, 4, 7 |

Note:
$LD_{50}$ was calculated from the mortality of ddy-mouse aged 6 weeks, 2 weeks after an inoculation of 0.005 ml of the serial-diluted medium in which the variants were cultured for 20 hours.

EXAMPLE 3

It was determined whether each variant secreted the biological activities derived from pertussis toxin, i.e., leukocytosis-promoting activity (LP), islet-activating activity (IA), and CHO cell-clustering activity in the cultured supernatant, by shake-culturing the variants in CLM medium for 2 days, concentrating the centrifuged supernatants with ⅔-saturated ammonium sulfate, according to the conventional method activities of each sample. The results are shown in Table 2. It was recognized that the variant 79G did not have a leukocytosis-promoting activity and islet-activating activity, as indicators of the biological activities of pertussis toxin, but caused a reaction of the polyclonal antibodies against pertussis toxin.

EXAMPLE 4

Figure 2:
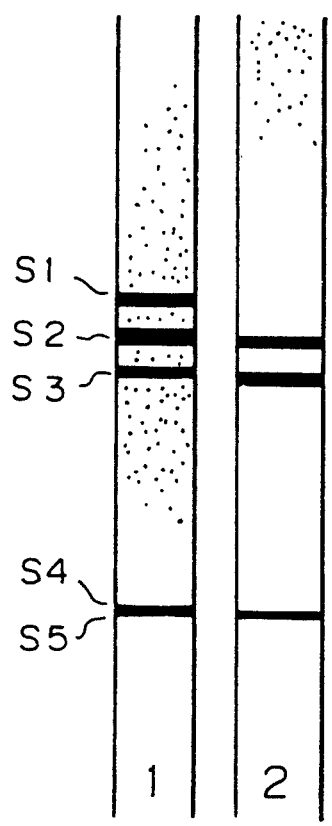
FIG. 2 is SDS-PAGE of proteins produced by the variant according to the present invention; and, FIG. 3 shows the results of an analysis by immunoblot of proteins according to the present invention.
Figure 3:
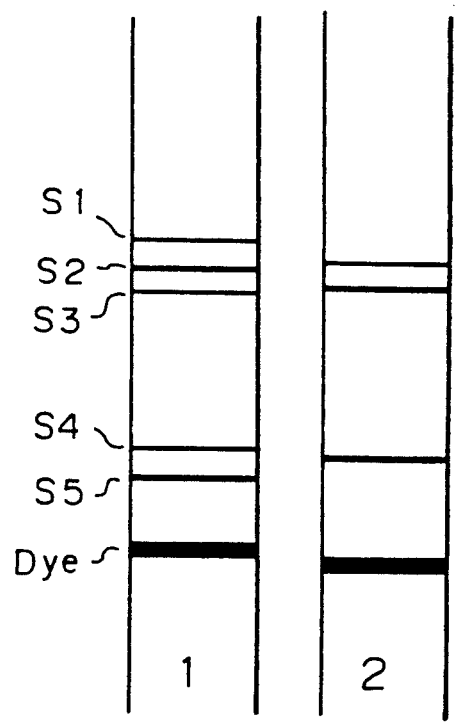

The following experiments were conducted to demonstrate the properties of the variant protein produced by the variant 79G. The supernatant, which was obtained from the shake-cultured medium of the variant 79G, was concentrated with ⅔-saturated ammonium sulfate, and then the concentrated culture supernatant was dialized against PBS 1M NaCl having been added thereto, the extract subjected to the anti-PT antibody-coupled Sepharose 4B, and the protein reacted with the anti-PT antibody using 3M KSCN was eluted to obtain a partially purified variant protein (PTMP). FIG. 2 illustrates the SDS-PAGE pattern of PTMP: wherein the control and, pertussis toxin (PT) is shown on the left, and the PTMP is shown on the right. This data demonstrates that the variant of the present invention is devoid of the protein band corresponding to S1. FIG. 3, which illustrates the patterns of reactivities between the protein and the anti-PT polyclonal antibody, clarifies the defect of the protein corresponding to subunit S1.

TABLE 2

| | Biological activities derived from supernatants of liquid medium cultured with the variants | | | |
|---|---|---|---|---|
| | PT activity (%) | | | |
| Strain | CHO 1) | LP 2) | IA 3) | aPT-ELISA |
| 19C | <0.01 | <0.3 | <0.05 | <0.5 |
| 102B | <0.01 | <0.3 | <0.05 | <0.5 |
| 35C | 0.6 | 2.5 | 1.0 | 2.5 |
| 79G | <0.01 | <0.3 | <0.05 | 25 |
| 74E | <0.01 | <0.3 | <0.05 | <0.5 |
| 19H | 100 | 79 | 68 | 100 |
| Tohama (wild) | 100 | 100 | 100 | 100 |

Note:
1) CHO cell-clustering activity.
2) leuko-cytosis-promoting activity,
3) islet-activating activity

EXAMPLE 5

It was determined whether the antibody against the variant protein was able to induce the neutralizing antibody against the native pertussis toxin by immunizing the mice with the partially purified variant protein following the treatment of alum-adjuvant, and obtaining the anti-PTMP anti-serum from the mice. Then, it was determined whether the serum could neutralize the biological activities, particularly the LP, HS, IA, CHO cell-clustering activity, etc. According to the previously mentioned method, the serum (anti-79G-PTMP) and the test PT appropriately diluted were mixed as a control of the anti-native PT antibody at the ratio of 1:1, reacted at room temperature for 30 min. or more and then administered to the mice (10/group) to determine the neutralizing activities. The results are shown in Table 3.

TABLE 3

| | PT activity-neutralizing capacity of anti-79G-PTMP antibody on mice | | | | |
|---|---|---|---|---|---|
| | Serum Dilution | LP act. WBC/μl | HS act. % Death | IA act. Insulin μU/ml | Anti-CC act. U/ml |
| Anti-79G-PTMP + Test toxin | × 2 | 3,600 | 0 | 27 | |
| | × 10 | 1,600 | 50 | 460 | 1,050 |
| | × 50 | 23,200 | 100 | 1,625 | |
| | × 250 | 34,200 | 100 | 2,200 | |
| Anti-PT + Test toxin | × 10 | 2,000 | 50 | 35 | |
| | × 50 | 14,600 | 100 | 1,275 | 1,050 |
| | × 250 | 30,000 | 100 | 2,400 | |
| Test toxin | — | 28,600 | 100 | 1,875 | — |
| PBS | — | 0 | 0 | 43 | — |

The anti-79G-PTMP antibody neutralized LP, HS, IA, and CHO cell-clustering activity in the same way as the anti-PT antibody against native PT, and the degrees of neutralization were almost at the same level. This means that the anti-79G-PTMP antibody without the anti-S1 antibody is able to neutralize these biological activities in the same way as the anti-native PT antibody with the anti-S1 antibody.

EXAMPLE 6

The activity of 79G-PTMP vaccine by the conventional intracerebral inoculation to mice (the ic challenge), using native PT as the control, was determined. Both antibodies were treated with alum-adjuvant, and mice aged 4 weeks (10 mice per group) were conducted the ic challenge of pertussis virulent strain (18-323) 3 weeks after immunization of the mice. The survival rates after the challenge are shown in Table 4. The experimental mouse infectious method demonstrated that the antigen 79G-PTMP provided a sufficient protective effect on the mice.

TABLE 4

| | Protection test of mice by the ic challenge of 79G-PTMP | |
|---|---|---|
| Antigen | Immun, dose μg/mouse | Survival % |
| 79G-PTMP | 2.5 | 90 |
| | 0.5 | 70 |
| | 0.1 | 10 |
| PT | 7.5 | 100 |
| | 1.5 | 100 |
| | 0.3 | 60 |
| PBS | 0 | 0 |

EXAMPLE 7

To examine the activity of 79G-PTMP vaccine, a passive protection test was carried out by lethal aerosol challenge to new-born mice aged 3 days using the anti-79G-PT antibody. The results are shown in Table 5. The aerosol challenge to mice demonstrated that anti- 79G-PTMP provide a similar protective effect to that of anti-PT.

TABLE 5

Passive protection test of the anti-79G-PT antibody against lethal aerosol challenge

| Antibody | Dose per mouse[1] | Survival rate[2] | $PD_{50}$[3] |
|---|---|---|---|
| 79G-PT | 100 | 15/15 | 9.6 |
|  | 20 | 13/15 | (5.0–18.0) |
|  | 4 | 1/15 |  |
| PT | 50 | 14/15 | 10.0 |
|  | 10 | 9/15 | (5.3–18.9) |
|  | 2 | 0/15 |  |
| PBS | — | 0/15 |  |

Note:
[1] Doses are expressed as PT-ELISA units.
[2] Number of surviving/total mice 21 days after aerosol challenge.
[3] The 50% protective doses ($PD_{50}$) are expressed as PT-ELISA units. The 95% confidence intervals are indicated in parentheses.

We claim:
1. A Bordetella pertussis variant which produces a pertussis toxin protein lacking ADP-ribosyltransferase activity associated with the S1 subunit.
2. The Bordetella pertussis variant according to claim 1, which is deposited in the Fermentation Research Institute with International Deposition N. FERM BP-1902.
3. The variant of claim 1 wherein said protein lacks an S1 subunit.
4. The variant of claim 1 wherein said protein comprises an S1 subunit that is not functional.
5. A pertussis toxin mutant protein lacking ADP-ribosyltransferase activity associated with the S1 subunit, and produced by a Bordetella pertussis variant.
6. A pertussis vaccine prepared by using a pertussis toxin mutant protein lacking ADP-ribosyltransferase activity associated with the S1 subunit.

* * * * *